United States Patent [19]

Coy et al.

[11] 4,431,635
[45] Feb. 14, 1984

[54] LH-RH ANTAGONISTS

[76] Inventors: David H. Coy, 4319 Perrier St., New Orleans, La. 70115; Andrew V. Shally, 5025 Kawanee Ave., Metairie, La. 70002

[21] Appl. No.: 341,137

[22] Filed: Jan. 20, 1982

Related U.S. Application Data

[63] Continuation-in-part of Ser. No. 115,249, Jun. 2, 1980, Pat. No. 4,317,315.

[51] Int. Cl.$^3$ .................... H61K 37/00; C07C 103/52
[52] U.S. Cl. .......................... 424/177; 260/112.5 LH
[58] Field of Search ............... 260/112.5 LH; 424/177

[56] References Cited

U.S. PATENT DOCUMENTS

| | | | |
|---|---|---|---|
| 3,928,307 | 12/1975 | Foell et al. | 260/112.5 LH |
| 3,933,782 | 1/1976 | Yardley | 260/112.5 LH |
| 4,018,726 | 6/1977 | Schally et al. | 260/112.5 LH |
| 4,124,703 | 11/1978 | Dutta et al. | 260/112.5 LH |
| 4,253,997 | 3/1981 | Sarantakis | 260/112.5 LH |
| 4,317,815 | 3/1982 | Cory et al. | 260/112.5 LH |

*Primary Examiner*—Delbert K. Phillips
*Attorney, Agent, or Firm*—Wegner & Bretschneider

[57] ABSTRACT

Disclosed herein are peptide analogs of the luteinizing hormone releasing hormone (LH-RH) which are potent antagonists of LHRH. The analogs differ in structure from LH-RH by having different amino acid residues at positions 1, 2 and 6, and optionally at positions 3 and 10. Methods for preparing and using these analogs are described.

9 Claims, No Drawings

LH-RH ANTAGONISTS

This is a continuation-in-part of copending application Ser. No. 115,249 filed June 2, 1980, now U.S. Pat. No. 4,317,815.

This invention relates to novel peptides which are antagonists of the luteinizing hormone releasing hormone (LH-RH), which has the structure: p-Glu-His-Trp-Ser-Tyr-Gly-Leu-Arg-Pro-Gly-NH$_2$. More specifically, this invention relates to luteinizing hormone releasing factor (LH-RH) analogs, salts thereof, to processes and intermediates for preparing these analogs, and to pharmaceutical compositions and methods of use pertaining to these analogs.

The LH-RH analogs of this invention differ in structure from LH-RH by having the amino acid residues at positions 1, 2 and 6, and optionally at positions 3 and 10, replaced with other amino acid residues.

For several years investigators have been searching for selective, potent antagonists of the LH-RH decapeptide. See the review article by D. H. Coy and A. V. Schally, Annals of Clinical Research, 10, 139 (1978). The high degree of interest in such antagonists is due to their usefulness in the endocrine and cancer fields. A great number of compounds have been prepared as potential LH-RH antagonists but most of these compounds lack potency or are mixed agonists and antagonists of the LH-RH decapeptide. The most interesting antagonists to date have been compounds having a modified structure of LH-RH. For instance, [D-PHe$^2$]-LH-RH, R. A. W. Rees et al., J.Med.Chem., 17, 1016 (1974); [D-Phe$^2$, D-Phe$^6$]-LH-RH, [D-Phe$^2$, Phe$^3$, D-Phe$^6$]-LH-RH and [D-Phe$^2$, D-Trp$^3$, D-Phe$^6$]-LH-RH, D. H. Coy et al., in "Peptides 1976", A. Loffet, Ed., Editions de l'Universite de Bruxelles, Brussels, Belgium, 1977, p. 463; [D-p-F-Phe$^2$-D-Ala$^6$]-LH-RH, C. W. Beattie et al., J.Med.Chem., 18, 1247 (1975) and [Ac-D-Phe$^1$, D-Phe$^2$, D-Trp$^{3,6}$]-LH-RH, K. Channabasavaiah and J. M. Stewart, Biochem.Biophys. Res.-Commun., 86, 1266 (1979).

The present invention provides pure LH-RH antagonists that are more potent than any of the LH-RH antagonists reported to date.

The compounds of this invention, i.e. the LH-RH analogs, are represented by formula I X-R$^1$-R$^2$-R$^3$-Ser-Tyr-R$^4$-Leu-Arg-Pro-R$^5$-NH$_2$ (I)

in which X is hydrogen, lower alkanoyl, HOOC-(CH$_2$)$_n$-CO wherein n is an integer from 2 to 6, benzoyl or the acyl portion of glycine or a D- or L-amino acid; R$^1$ is Gly, L-Ala, D-Ala, D-Trp, D-Phe or D-Phe having a substituent in para position selected from halo, nitro, amino, methyl, cyano, trifluoromethyl, hydroxy and methoxy; R$^2$ is D-Phe having a substituent in the para position of the phenyl group selected from the group consisting of halo, nitro, amino, methyl, cyano, trifluoromethyl, hydroxy and methoxy; R$^3$ is D-Trp, L-Trp or L-Phe; R$^4$ is D-Trp, D-Phe or D-Phe having a substituent in the para position of the phenyl group selected from the group consisting of halo, nitro, amino, methyl, cyano, trifluoromethyl, hydroxy and methoxy; and R$^5$ is Gly or D-Ala.

A preferred group of compounds of formula I is one in which X is hydrogen, lower alkanoyl, HOOC-(CH$_2$)$_n$-CO wherein n is an integer from 2 to 6, benzoyl or the acyl portion of alanine, arginine, asparagine, cysteine, glutamine, glycine, histidine, isoleucine, leucine, lysine, methionine, ornithine, phenylalanine, proline, serine, threonine, tryptophan, tyrosine or valine; R$^1$ is D-Trp, D-Phe or D-p-Y-Phe wherein Y is selected from the group consisting of halo, nitro, amino, methyl, cyano, trifluoromethyl, hydroxy and methoxy; R$^2$ is D-p-Y-Phe in which Y is as defined herein; R$^3$ is D-Trp; R$^4$ is D-Trp, D-Phe or D-p-Y-Phe in which Y is as defined herein; and R$^5$ is D-Ala.

Another preferred group of the compounds of formula I is that in which X is hydrogen, lower alkanoyl or HOOC-(CH$_2$)$_n$-CO wherein n is as defined herein; R$^1$ is D-Trp,D-Phe or D-p-halo-Phe; R$^2$ is D-p-halo-Phe; R$^3$ is D-Trp; R$^4$ is D-Trp or D-Phe; and R$^5$ is D-Ala.

Still another preferred group of the compounds of formula I is that in which X is acetyl or HOOCCH$_2$CH$_2$CO; R$^1$ is D-Trp,D-Phe or D-p-Cl-Phe; R$^2$ is D-p-Cl-Phe; D-p-Br-Phe or D-p-F-Phe; R$^3$ is D-Trp; R$^4$ is D-Trp or D-Phe; and R$^5$ is D-Ala.

The therapeutically acceptable salts of the compound of formula I are included within the scope of this invention.

The compounds of formula I are prepared by conventional peptide synthesis or by solid phase techniques.

In general, the peptides I may be prepared by removal of the protective group(s) from a peptide of formula IA:

X$^1$-R$^1$-R$^2$-R$^3$-Ser(R$^6$)-Tyr(R$^7$)-R$^4$-Leu-Arg(N$^G$-R$^8$)-Pro-R$^5$-NH$_2$ wherein R$^1$, R$^2$, R$^3$, R$^4$ and R$^5$ are as herein defined, X$^1$ has the same meaning as X as herein defined but in addition may represent an N-protective group or an N-protected acyl portion of a D- or L-amino acid, and R$^6$, R$^7$ and R$^8$ are each hydrogen, or a protective group, with the proviso that at least one of the radicals X$^1$, R$^6$, R$^7$ or R$^8$ is or contains a protective group, and, if desired, followed by N-acylation of the resulting compound of formula I, wherein X is hydrogen.

The compounds of formula I may also be prepared by a process, which comprises:

(a) reacting a compound of the formula II:

X-R$^1$-R$^2$-R$^3$-Ser(R$^6$)-Tyr(R$^7$)-R$^4$-Leu-Arg(N$^G$-R$^8$)-Pro-R$^5$-A (II)

wherein X, R$^1$, R$^2$, R$^3$, R$^4$, R$^5$, R$^6$, R$^7$ and R$^8$ are as defined herein and A is

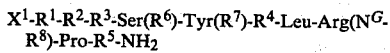

with a reagent capable of cleaving off the resin support and the anchoring radical, i.e.

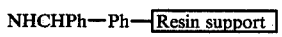

or (b) subjecting the compound of the formula II wherein X, R$^1$, R$^2$, R$^3$, R$^4$, R$^5$, R$^6$, R$^7$ and R$^8$ are as defined herein and A is

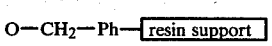

to ammonolysis, to obtain in both cases (a and b) a peptide of the formula III:

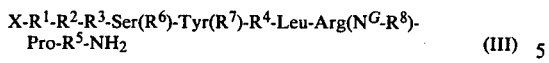

X-R$^1$-R$^2$-R$^3$-Ser(R$^6$)-Tyr(R$^7$)-R$^4$-Leu-Arg(N$^G$-R$^8$)-Pro-R$^5$-NH$_2$     (III)

in which X, R$^1$, R$^2$, R$^3$, R$^4$, R$^5$, R$^6$, R$^7$ and R$^8$ are as defined herein; followed by, when the compound of formula III is different from the compound of formula I, reacting the compound of formula III with a reagent capable of removing the protecting groups without affecting the compound of formula I.

The compounds of formulae IA and II, and the compound of formula III when different from the compound of formula I, also are included within the scope of this invention.

A further aspect of the invention relates to intermediates linked to a solid resin support and having a protected α-amino group. These intermediates are represented by the formula IV:

R$^9$-R$^1$-R$^2$-R$^3$-Ser(R$^6$)-Tyr(R$^7$)-R$^4$-Leu-Arg(N$^G$-R$^8$)-Pro-R$^5$-A in which R$^1$ to R$^8$, inclusive, are as defined herein and R$^9$ is an α-amino protective group known to be useful in the art of the stepwise synthesis of polypeptides, suitable groups being listed hereinafter, and A is selected from the group consisting of

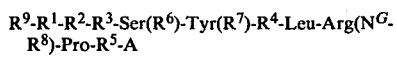

NH—CHPh—Ph—[resin support]    and

OCH$_2$—Ph—[resin support]

A gonadotropin antagonizing pharmaceutical composition is provided by admixing the compound of formula I with a pharmaceutically acceptable carrier.

Also provided is a method for relieving complications from the physiological availability of pituitary gonadotropins in a mammal, which involves administering to the mammal a gonadotropin antagonizing dose of the compound of formula I.

The term "lower alkanoyl" as used herein means straight chain alkanoyl radicals containing one to six carbon atoms, e.g. formyl, acetyl, propionyl, butyryl and hexanoyl, and branched chained alkanoyl radicals containing four to six carbon atoms, e.g. isobutyryl and pivaloyl.

The term "lower alkanoic acid" as used herein means both straight and branched chain alkanoyl radicals containing two to six carbon atoms and includes acetic acid, propionic acid, pivalic acid, hexanoic acid and the like.

The term "organic proton acceptor" as used herein means the organic bases, or amines for instance, triethylamine, pyridine, N-ethylmorpholine, imidazole and the like.

The term "halo" includes chloro, bromo, fluoro and iodo.

The term "amino acid" as used herein means the well known and reasonably accessible amino acids which are described in general textbooks on peptide chemistry; for instance, see K. D. Kopple, "Peptides and Amino Acids", W. A. Benjamin Inc., New York and Amsterdam, 1966, pp. 4–7.

The term "acyl portion" of an amino acid means a radical derived from the corresponding amino acid by eliminating the hydroxyl of the carboxy group.

The term "amino acid residue" refers to a radical derived from the corresponding amino acid by eliminating the hydroxyl of the carboxy group and one hydrogen of the amino group.

N$^G$ means the side chain nitrogen atoms of arginine.

The symbol Ph— means "phenyl" and the symbol —Ph— means 1,4-phenylene.

Ac means "acetyl". Succ means "HOOC-(CH$_2$)$_2$-CO", i.e. succinyl, a 3-carboxy-1-propionyl radical.

"A" is an anchoring bond linked to a solid resin (resin support) used in solid phase synthesis and is selected from the class consisting of:

—NH—CHPh—Ph—[resin support]    and

OCH$_2$—Ph—[resin support].

The term "anchoring radical" means that portion of A which is —CH—Ph—Ph— or —CH$_2$—Ph.

In general, the abbreviations used herein for designating the amino acids and the protective groups are based on recommendations of the IUPACIUB Commission on Biochemical Nomenclature, see Biochemistry II, 1726 (1972). For instance, t-Boc represents t-butyloxycarbonyl, Z represents benzyloxycarbonyl, Tos represents tosyl and Bzl represents benzyl. The abbreviations used herein for the various amino acids are Ala, alanine; Arg, arginine, Gly, glycine; Leu, leucine; Phe, phenylalanine; Pro, proline; Ser, serine; Trp, tryptophan; and Tyr, tysosine. All amino acids described herein are in the L-series unless stated otherwise, e.g. D-Ala is a D-alanyl residue, D-Phe is a D-phenylalanyl residue and D-Trp is a D-tryptophyl residue.

The LH-RH analogs of this invention can be obtained in the form of an acid addition salt. Examples of salts are those with organic acids, e.g. acetic, lactic, succinic, benzoic, salicylic, methanesulfonic or p-toluenesulfonic acid, as well as polymeric acids, such as tannic acid or carboxymethyl cellulose, and salts with inorganic acids, such as hydrohalic acids, e.g. hydrochloric acid, or sulfuric acid, or phosphoric acid. If desired, a particular acid addition salt is converted into another acid addition salt, e.g. a salt with a non-toxic, therapeutically acceptable acid, by treatment with the appropriate ion exchange resin in the manner described by R. A. Boissonnas, et al., Helv.Chim.Acta., 43, 1349 (1960). Suitable ion exchange resins are cellulose based cation exchangers, for example carboxymethylcellulose or chemically modified, cross linked dextran cation exchangers, for example the chemically modified, cross-linked dextran cation exchanger sold under the trade mark Sephadex C, and strongly basic anion exchange resins, for example those listed by J. P. Greenstein and M. Winitz in "Chemistry of the Amino Acids", John Wiley and Sons, Inc., New York and London, 1961, Vol. 2, p. 1456. These therapeutically acceptable acid addition salts are included within the scope of this invention.

The compounds of formula I in which HOOC-(CH$_2$)$_n$-CO wherein n is an integer from 2 to 6 form salts with suitable therapeutically acceptable inorganic and organic bases. These derived salts possess the same activity as the parent acid and are included with the scope of this invention. The acid is transformed in excellent yield into the corresponding therapeutically acceptable salt by neutralization of said acid with the appropriate inorganic or organic base. Suitable inorganic bases to form these salts include, for example, the hydroxides, carbonates, bicarbonates or alkoxides of the therapeutically acceptable alkali metals or alkaline earth metals, for example, sodium, potassium, magnesium, calcium and the like. Suitable organic bases include the following amines; lower mono-, di- and trialkylamines, the alkyl radicals of which contain up to three carbon atoms, such as methylamine, dimethylamine, trimethylamine, ethylamine, di- and triethylamine, N-methyl-N-ethylamine, and the like; and mono-, di- and trialkanolamines, the alkanol radicals of which contain up to three carbon atoms, for example, mono-, di- and triethanolamine.

With reference to the compound of formula II, X-$R^1$-$R^2$-$R^3$-Ser($R^6$)-Tyr($R^7$)-$R^4$-Leu-Arg($N^G$-$R^8$)-Pro-$R^5$-A, and the compound of formula III, X-$R^1$-$R^2$-$R^3$-Ser($R^6$)-Tyr($R^7$)-$R^4$-Leu-Arg($N^G$-$R^8$)-Pro-$R^5$-$NH_2$, in a preferred embodiment X, $R^1$ to $R^5$ inclusive, and A are as defined herein, $R^6$ is a protective group for the hydroxyl group of serine and is selected from the group of 2-bromo-benzyloxycarbonyl, benzyl, acetyl, tosyl, benzoyl, tert-butyl, tetrahydropyra-2-yl, trityl, 2,4-dichlorobenzyl and benzyloxycarbonyl; $R^7$ is hydrogen or a protective group for the hydroxyl of tyrosine selected from the group defined hereinbefore for $R^6$, and $R^8$ is a protective group for the Nδ, Nω, and Nω' nitrogen atoms of arginine selected from the group consisting of tosyl, nitro, benzyloxycarbonyl and adamantyloxycarbonyl. In another preferred embodiment with reference to the compounds IA, II and III, the seryl and tyrosyl residues are not protected and the arginine residue is protected in the form of a strong acid addition salt, e.g., the hydrochloric acid, p-toluenesulfonic acid or sulfuric acid addition salt.

The valuable LH-RH antagonizing property of the compounds of this invention are demonstrated by standard pharmacological procedures. For example, this activity can be demonstrated in the test described by A. de la Cruz et al., Science, 191, 195 (1976). More explicity, the assay is performed using mature female rats (Charles River Breeding Laboratories, Boston, Mass., U.S.A.) weighing about 200 g and exhibiting normal four-day cycles. The analogs are administered in 20% propylene glycol in physiologic saline (see Table II) or as a suspension in corn oil (see Table I) at 12 noon of the day of proestrus. On the following day, the rats are sacrificed, their fallopian tubes and uteri flushed with saline and the washes examined for ova.

The test results for several analogs are given in Table II. In Table I, a comparison, between the compound of formula I in which X is acetyl, $R^1$ is D-Phe, $R^2$ is D-p-Cl-Phe, $R^3$ is D-Trp, $R^4$ is D-Trp and $R^5$ is Gly, the title compound of Example 7, and the compound of the prior art, [Ac-D-$Phe^1$, D-$Phe^2$, D-$Trp^{3,6}$]-LH-RH, noted hereinbefore, is shown. As noted above, a different carrier is used for administering the compounds in Table I than in Table II.

TABLE I

| Comparative antiovulatory activity | | |
|---|---|---|
| Peptide | Dose (mcg) | % Blockade of Ovulation |
| [Ac—D-$Phe^1$, D-p-Cl—$Phe^2$, D-$Trp^{3,6}$]—LH—RH | 31 | 100 |
| | 15 | 100 |
| [Ac—D-$Phe^1$, D-$Phe^2$, D-$Trp^{3,6}$]— | 250 | 100 |

TABLE I-continued

| Comparative antiovulatory activity | | |
|---|---|---|
| Peptide | Dose (mcg) | % Blockade of Ovulation |
| LH—RH* | 100 | 40 |

*K. Channabasavaiah and J. M. Stewart, Biochem. Biophys. Res. Commun., 86, 1226 (1979).

TABLE II

| Antiovulatory activity of compounds of formula I | | |
|---|---|---|
| Peptide | Dose (mg) | % Blockade of Ovulation |
| [D-$Phe^1$, D-p-Cl—$Phe^2$, D-$Trp^3$, D-$Phe^6$]—LH—RH | 0.25 | 82 |
| | 0.125 | 11 |
| [D-$Phe^1$, D-p-Br—$Phe^2$, D-$Trp^3$, D-$Phe^6$]—LH—RH | 0.25 | 50 |
| [D-$Phe^1$, D-p-F—$Phe^2$, D-$Trp^3$, D-$Phe^6$]—LH—RH | 0.25 | 10 |
| [Succ-D-$Phe^1$, D-p-Cl—$Phe^2$, D-$Trp^3$, D-$Phe^6$]—LH—RH | 0.125 | 80 |
| | 0.062 | 50 |
| [Ac—D-$Phe^1$, D-p-Cl—$Phe^2$, D-$Trp^{3,6}$] LH—RH | 0.062 | 100 |
| | 0.031 | 64 |
| [N—Ac—D-p-Cl—$Phe^{1,2}$, D-$Trp^{3,6}$]—LH—RH | 0.015 | 70 |
| [N—Ac—D-$Trp^{1,3,6}$, D-p-Cl—$Phe^2$]—LH—RH | 0.015 | 90 |
| [N—Ac—D-$Phe^1$, D-p-Cl—$Phe^2$, D-$Trp^{3,6}$, D-$Ala^{10}$]—LH—RH | 0.015 | 100 |
| [N—Ac—D-p-Cl—$Phe^{1,2}$, D-$Trp^3$, D-$Phe^6$, D-$Ala^{10}$]—LH—RH | 0.0075 | 88 |
| [N—Ac—D-$Trp^1$, D-p-Cl—$Phe^2$, D-$Trp^3$, D-$Phe^6$, D-$Ala^{10}$]—LH—RH | 0.0075 | 75 |
| | 0.0050 | 38 |
| [N—Ac—D-pF—$Phe^1$, D-p-Cl—$Phe^2$, D-$Trp^{3,6}$, D-$Ala^{10}$]—LH—RH | 0.0075 | 50 |
| [N—Ac—$Ala^1$, D-p-Cl—$Phe^2$, D-$Trp^{3,6}$, D-$Ala^{10}$]—LH—RH | 0.010 | 18 |

The LH-RH antagonizing properties of the compounds of this invention make the compounds useful in human and veterinary practice. For instance, the compounds of formula I find use as agents for relieving the complications from the undesirable physiological availability of pituitary gonadotropins in a mammal. Such complications include precocious puberty; hormone dependent tumors such as malignant and benign prostatic tumors, and mammary, ovarian and testicular tumors; hirsutism; acne; amenorrhea, e.g. secondary amenorrhea; endometriosis, and ovarian and mammary cystic diseases in both animals and humans. The compounds of formula I also are useful for regulating ovulation, thus rendering them useful agents for controlling fertility, e.g. as precoital or postcoital contraceptives, for synchronizing estrus in livestock and for improving the "rhythm" method. Also, the compounds are useful for regulating the human menopausal gonadotropin, follicle-stimulating hormone (FSH) and luteinizing hormone (LH) during perimenopausal and postmenopausal periods in women.

When the compound of formula I, preferably in the form of an acid addition salt, is employed in human or veterinary medicine, it is administered systemically, either orally or by subcutaneous or intramuscular injection, or by sublingual, nasal, or vaginal administration, in compositions in conjunction with a pharmaceutically acceptable vehicle or carrier.

The dosage of the compounds of formula I will vary with the form of administration and with the particular patient under treatment. Generally, treatment is initiated with small dosages substantially less than the optimum dose of the compound. Thereafter, the dosage is increased by small increments until the optimum effect under the circumstances is reached. In general, the compound obtained by the process is most desirably administered at a concentration level that generally will inhibit release of LH and of FSH without causing any harmful or deleterious side effects, and preferably at a level that is in a range of from about 10 mcg to about 1000 mcg per kilogram body weight, although, as aforementioned, variations will occur. However, a dosage level that is in the range of from about 25 mcg to about 250 mcg per kilogram body weight is most desirably employed in order to achieve effective results.

For administration by the nasal route as drops or spray it is preferred to use the compound of formula I in solution in a sterile aqueous vehicle which may also contain other solutes such as buffers or preservatives, as well as sufficient quantities of pharmaceutically acceptable salts or of glucose to make the solution isotonic. Doses by the intranasal route range from 100 mcg to 10.0 mg/kg, or preferably 100 mcg to 1.0 mg/kg of body weight.

The compound of formula I also may be administered as nasal or vaginal powders or insufflations. For such purposes the decapeptide is administered in finely divided solid form together with a pharmaceutically acceptable solid carrier; for example, a finely divided polyethylene glycol for instance the polyethylene glycol sold under the trade mark "Carbowax 1540"; finely divided lactose; or preferably for vaginal administration, very finely divided silica, for instance, the silica sold under the trade mark "Cab-O-Sil". Such compositions may also contain other excipients in finely divided solid form such as preservatives, buffers, or surface active agents.

For sublingual or vaginal administration, the compound is formulated preferably in solid dosage forms such as sublingual tablets or vaginal inserts or suppositories with sufficient quantities of solid excipients such as starch, lactose, certain types of clay, buffers, and lubricating, disintegrating, or surfaceactive agents, or with semi-solid excipients commonly used in the formulation of suppositories. Examples of such excipients are found in standard pharmaceutical texts, e.g. in Remington's Pharmaceutical Sciences, Mack Publishing Company, Easton, Pa., 1970.

It is often desirable to administer the compounds of formula I continuously over prolonged periods of time in long-acting, slow-release, or depot dosage forms. Such dosage forms may either contain a pharmaceutically acceptable salt of the compound having a low degree of solubility in body fluids, for example one of those salts described below, or they may contain the compound in the form of a water-soluble salt together with a protective carrier which prevents rapid release. In the latter case, for example, the compound may be formulated with a non-antigenic partially hydrolized gelatin in the form of a viscous liquid; or it may be adsorbed on a pharmaceutically acceptable solid carrier, for example, zinc hydroxide, and may be administered in suspension in a pharmaceutically acceptable liquid vehicle; or the decapeptide may be formulated in gels or suspensions with a protective non-antigenic hydrocolloid, for example sodium carboxymethylcellulose, polyvinylpyrrolidone, sodium alginate, gelatine, polygalacturonic acids, for example, pectin, or certain mucopolysaccharides, together with aqueous or non-aqueous pharmaceutically acceptable liquid vehicles, preservatives, or surfactants. Examples of such formulations are found in standard pharmaceutical texts, e.g.

Remington's Pharmaceutical Sciences, cited above. Long-acting, slow-release preparations of the compound may also be obtained by microencapsulation in a pharmaceutically acceptable coating material, for example gelatine, polyvinyl alcohol or ethyl cellulose. Further examples of coating materials and of the processes used for microencapsulation are described by J. A. Herbig in "Encyclopedia of Chemical Technology", Vol. 13, 2nd ed., Wiley, New York, 1967, pp. 436–456. Such formulations, as well as suspensions of salts of the compound which are only sparingly soluble in body fluids, are designed to release from about 10–1000 mcg of the compound per kilogram body weight per day, and are preferably administered by intramuscular injection. Alternatively, some of the solid dosage forms listed above, for example certain sparingly watersoluble salts or dispersions in or adsorbates on solid carriers of salts of the compound, for example dispersions in a neutral hydrogel of a polymer of ethylene glycol methacrylate or similar monomers, cross-linked as described in U.S. Pat. No. 3,551,556, issued Dec. 29, 19870 to K. Kliment, et al., may also be formulated in the form of pellets releasing about the same amounts as shown above and may be implanted subcutaneously or intramuscularly.

Alternatively, slow-release effects over prolonged periods of time may also be obtained by administering the compound obtained by the process of this invention in an intra-vaginal device or in a temporary implant, for example a container made of a non-irritating silicone polymer such as polysiloxane, a suitable polysiloxane is sold under the trade mark "Silastic", or of a neutral hydrogel of a polymer as described above, possessing the required degree of permeability to release from about 0.1 mcg to about 50 mcg per kilogram body weight per day. Such intravaginal or implant dosage forms for prolonged administration have the advantage that they may be removed when it is desired to interrupt or to terminate treatment.

In selecting a particular side chain protective group to be used in the synthesis of the present decapeptide, the following rules should be followed: (a) the protective group must be stable to the reagent and under the reaction conditions selected for removing the α-amino protective group at each step of the synthesis, (b) the protective group must retain its protecting properties (i.e., not be split off under coupling connditions), and (c) the side chain protective group must be removable upon the completion of the synthesis of the peptide containing the desired amino acid sequence under reaction conditions that will not alter the peptide chain.

With reference to α-amino protective groups for instance $R^9$, suitable protective groups include (1) aliphatic urethan protective groups illustrated by t-butyloxycarbonyl, diisopropylmethoxycarbonyl, biphenylisopropyloxycarbonyl, isopropyloxycarbonyl, t-amyloxycarbonyl, ethoxycarbonyl and allyloxycarbonyl; (2) cycloalkyl urethan type preotective groups illustrated by cyclopentyloxycarbonyl, adamantyloxycarbonyl, d-isobornylcarbonyl and cyclohexyloxycarbonyl; and nitrophenylsulfenyl; tritylsulfenyl; α,α-dimethyl-3,5-dimethoxybenzyloxycarbonyl; and trityl. The preferred α-amino protective groups are selected from the group consisting of t-butyloxycarbonyl, cyclopentyloxycarbonyl, t-amyloxycarbonyl, d-isobornyloxycarbonyl, o-nitrophenylsulfenyl, biphenylisopropyloxycarbonyl, and α,α-dimethyl-3,5-dimethoxybenzyloxycarbonyl.

Using solid phase techniques the synthesis is commenced from the C-terminal end of the peptide using an α-amino protected amino acid linked to a solid resin. Such a starting material is prepared for example, by attaching an α-amino protected glycine to a benzhydrylamine resin, a chloromethylated resin or a hydroxymethyl resin, the former being preferred. The preparation of a benzhydrylamine resin is described by P. Rivaille, et al., Helv. Chim. Acta., 54, 2772 (1971) and the preparation of the hydroxymethyl resin is described by M. Bodanszky and J. T. Sheehan, Chem. Ind. (London), 38, 1597 (1966). A chloromethylated resin is commercially available from Bio Rad Laboratories, Richmond, California. In using the benzhydrylamine resin, an amide anchoring bond is formed with the α-amino protected glycine or D-alanine, illustrated as follows for glycine:

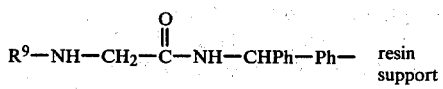

This permits the C-terminal amide function to be obtained directly after the amino acid sequence in the synthesis is completed by cleaving off the resin support and anchoring radical of the linked peptide to form the amino acid amide at the C-terminal portion of the desired compound. In this instance the use of hydrogen fluoride for cleaving off the resin support also removes the side chain protective groups to give the decapeptide of this invention.

When the other resins are used, the anchoring bond is the benzylester group as illustrated hereinbefore. In this instance a convenient procedure for converting the linked protected peptide to the C-terminal amide is to ammonolize the protected peptide off the resin and then remove the protective groups of the resulting amide by treatment with sodium in liquid ammonia or by the hydrogen fluoride cleavage. An alternative procedure would be to cleave by transesterification with a lower alkanol, preferably methanol or ethanol, in the presence of triethylamine and then convert the resulting ester into an amide and subsequently deprotect as described above. See also J. M. Steward and J. D. Young, "Solid Phase Peptide Synthesis", W. H. Freeman & Co., San Francisco, 1969, pp. 40–49.

More specifically, in an embodiment of the present invention, an α-amino protected amino acid; namely, an α-amino protected glycine, preferably t-butyloxycarbonylglycine; or an α-amino protected D-alanine, preferably t-butyloxycarbonyl-D-alanine; is coupled to the benzhydrylamine resin with the aid of a carboxy group activating compound, preferably, dicyclohexylcarbodiimide or diisopropylcarbodiimide. Following the coupling of the α-amino protected amino acid to the resin support, the α-amino protecting group is removed such as by using trifluoracetic acid in methylene chloride, trifluoracetic acid alone or hydrochloric acid in dioxane. The deprotection is carried out at a temperature between 0° C. and room temperature (i.e. 20° to 24° C.). Other standard cleavage reagents and conditions for removal of specific α-amino protecting groups may be used as described by E. Schroder and K. Lubke, "The Peptides", Vol. 1, Academic Press, New York, 1965, pp. 72–75. After removal of the α-amino protecting group, the remaining α-amino protected amino acids are coupled step-wise in the desired order to obtain the peptide. Each protected amino acid is introduced into the solid phase reactor in about a three-fold excess and the coupling is carried out in a medium of methylene chloride or mixtures of dimethylformamide in methylene chloride. In cases where incomplete coupling occurred, the coupling procedure is repeated before removal of the α-amino protecting group, prior to the coupling of the next amino acid to the solid phase reactor. The success of the coupling reaction at each stage of the synthesis is monitored by the ninhydrin reaction as described by E. Kaiser, et al., Analyt. Biochem., 34, 595 (1970). In this manner the compounds of formula II in which X is hydrogen is obtained.

After the desired amino acid sequence has been synthesized, the peptide is removed from the resin support by treatment with a reagent such as hydrogen fluoride which not only cleaves the peptide from the resin but also cleaves all remaining side chain protecting groups to obtain directly the peptide of formula I wherein X is hydrogen in the case where the benzhydrylamine resin was used.

Where a chloromethylated resin is used the peptide may be separated from the resin by transesterification with a lower alkanol, preferably methanol or ethanol, after which the recovered product is chromatographed on silica gel and the collected fraction subjected to treatment with ammonia to convert the lower alkyl ester, preferably the methyl or ethyl ester, to the C-terminal amide. In this manner the compounds of formula III in which X is hydrogen are obtained. The side chain protecting groups are then cleaved by procedures described above, for example by treatment with sodium in liquid ammonia or by hydrogen fluoride to give the corresponding compound of formula I wherein X is hydrogen.

The peptide compounds of formula I in which X is other than hydrogen are obtained by acylation of the corresponding compound of formula II or III in which X is hydrogen with the appropriate acylating agent, followed by cleaving the resin support together with the anchoring radical, and all the remaining side chain protecting groups of the acylated product by the procedures described above. Preferably, a lower alkanoic acid chloride or bromide or lower alkanoic anhydride in the presence of an organic proton acceptor, e.g. pyridine or imidazole, is used as the acylating agent to prepare the compounds of formula II or III in which X is lower alkanoyl. Likewise, in the presence of an organic proton acceptor, compounds of formula II or III in which X is HOOC-$(CH_2)_n$-CO or benzoyl are prepared using the acid chloride or acid bromide corresponding to the desired acyl radical X, e.g. succinyl chloride can be used for preparing compounds of formula II or III in which X is $HOOCCH_2CH_2CO$ and benzoyl chloride can be used to prepare the compounds of formula II or III in which X is benzoyl. The compound of formula II or III in which X is the acyl portion of a D- or L-amino acid are prepared conveniently by the "activated ester" coupling procedure. Accordingly, the amino acid corresponding to the desired acyl portion to be incorporated into the compound of formula II or III is converted into an activated ester. Descriptions of such carboxyl-activating groups are found in general textbooks of peptide chemistry; for example K. D. Kopple, "Peptides and Amino Acids", W. A. Benjamin, Inc., New York, 1966, pp. 45–51, and E. Schröder and K. Lübke, "The Peptides"; Vol. 1, Academic Press, New York, 1965, pp. 77–128. Examples of the activated form of the terminal carboxyl are acid chloride, anhydride, azide, activated ester, or O-acyl urea of a dialkylcarbodiimide. The following activated esters have proved to be particularly suitable in the process of this invention: 2,4,5-trichlorophenyl (represented by Tcp), pentachlorophenyl (represented by Pcp), p-nitro-phenyl (represented by Np); the 1-benzotriazolyl group (represented by Bt) or the succinimido group is also useful for such activation.

The peptide compounds of formula I in which X is hydrogen also are useful for preparing the compounds of formula I in which X is other than hydrogen by subjecting the former compound to the appropriate acylating agent.

Although a solid phase synthesis of the compound of formula I is disclosed herein, the preparation of the compound also can be realized by classical solution methods.

The following Examples illustrate further this invention. In the examples, the ratio noted in connection with a mixture of solvents refers to the relative proportion of the solvents with respect to volume.

EXAMPLE 1

D-Phenylalanyl-D-p-chlorophenylalanyl-D-tryptophyl-L-seryl (O-benzyl)-L-tyrosyl-D-tryptophyl-L-leucyl-L-arginyl($N^G$-tosyl)-L-prolyl-glycyl-benzhydrylamine resin Benzhydrylamine resin (1.0 g, 0.5 mmole) was placed in the reaction vessel of a Beckman Model 990 automatic peptide synthesizer programmed to carry out the following work cycle: (a) methylene chloride; (b) 33% trifluoroacetic acid in methylene chloride (2 times for 1 and 25 min each); (c) methylene chloride; (d) ethanol; (e) chloroform; (f) 10% triethylamine in chloroform (2 times for 3 min each); (g) chloroform; (h) methylene chloride.

The washed resin was stirred with t-butyloxycarbonyl glycine (263 g, 1.5 mmoles) in methylene chloride and diisopropylcarbodiimide (1.5 mmoles) was added. The mixture was stirred at room temperature for 1 hour and the amino acid resin was then washed successively with methylene chloride, ethanol and methylene chloride (3 times each). The protected, attached amino acid was then cycled through steps (b) through (h) in the above was program. The following amino acids (1.5 mmoles) were then coupled successively by the same cycle of events: t-Boc-L-proline, t-Boc-L-arginine ($N^G$-Tos); t-Boc-L-Leucine; t-Boc-D-tryptophan, t-Boc-L-tyrosine, t-Boc-L-serine (O-Bzl), t-Boc-D-tryptophan, t-Boc-D-p-chlorophenylalanine, t-Boc-D-phenylalanine. The completed resin with the N-terminal t-Boc group removed was washed with methanol and dried under reduced pressure whereupon 1.42 g of the title compound was obtained.

EXAMPLE 2

N-Acetyl-D-phenylalanyl-D-p-chlorophenylalanyl-D-tryptophyl-L-seryl(O-benzyl)-L-tyrosyl-D-tryptophyl-L-leucyl-L-arginyl ($N^G$-tosyl)-L-prolyl-glycyl-benzhydryl-amine resin Part (0.76 g) of the decapeptide resin, described in Example 1, was treated with 30 min with 30 ml of a solution of imidazole (5 g) and acetic anhydride (3.54 ml) in methylene chloride (100 ml). The acetylated peptide-resin was then washed with methylene chloride (3 times) and methanol (3 times) and dried in vacuo to give the title compound.

EXAMPLE 3

D-Phenylalanyl-D-p-bromophenylalanyl-D-tryptophyl-L-seryl (O-benzyl)-L-tyrosyl-D-phenylalanyl-L-leucyl-L-arginyl ($N^G$-tosyl)-L-prolyl-glycyl-benzhydrylamine resin The peptide resin was assembled on the same scale and under conditions described in Example 1, with exception that t-Boc-D-p-bromophenylalanine was incorporated in place of t-Boc-D-chlorophenylalanine and that t-Boc-phenylalanine was incorporated in place of t-Boc-D-tryptophan in position six of the chain. The completed, dry peptide resin of the title compound weighed 1.42 g.

EXAMPLE 4

D-Phenylalanyl-D-p-chlorophenylalanyl-D-tryptophyl-L-seryl (O-benzyl)-L-tryptophyl-D-phenylalanyl-L-leucyl-L-arginyl ($N^G$-tosyl)-L-prolyl-glycyl-benzhydrylamine resin The peptide was assembled on the same scale and under the conditions in Example 1, with the exception that t-Boc-phenylalanine was incorporated in place of t-Boc-D-tryptophan in position six of the chain. The completed, dry peptide-resin of the title compound weighed 1.41 g.

EXAMPLE 5

N-Succinyl-D-phenylalanyl-D-p-chlorophenylalanyl-D-tryptophyl-L-seryl(O-benzyl)-L-tyrosyl-D-phenylalanyl-L-leucyl-L-arginyl($N^G$-tosyl)-L-prolyl-glycyl-benzhydrylamine resin Part (0.76 g) of the decapeptide resin described in Example 4 was reacted with 30 ml of a solution of imidazole and succinyl chloride in methylene chloride for 30 minutes. The acetylated peptide-resin was then washed with methylene chloride and methanol, and dried in vacuo to give the title compound.

EXAMPLE 6

D-phenylalanyl-D-p-chlorophenylalanyl-D-tryptophyl-L-seryl-L-tyrosyl-D-tryptophyl-L-leucyl-L-arginyl-L-polyl-glycinamide, [D-Phe$^1$, D-p-Cl-Phe$^2$, D-Trp$^{3,6}$]-LH-RH Removal of the protecting groups and cleavage of decapeptide from the resin described in Example 1 was carried out by treatment of 0.7 g of material with hydrogen fluoride (20 ml), anisole (5 ml), and 1,4-dithiothreitol (50 mg) at 0° C. for 1 hour. The hydrogen fluoride was removed under a nitrogen stream and the peptide was precipitated by addition of diethyl ether.

The crude peptide was extracted with 50% acetic acid. The extract was subjected to gel filtration on a column (2.5×95 cm) of a fine grade, chemically modified cross-linked dextran, sold under the trade mark "Sephadex G-50", using 50% acetic acid as the eluant. Fractions shown to contain a major peak by UV absorption at 280 nm were pooled and evaporated to dryness.

The residual oil was applied to a column (1.5×145 cm) of silica gel and eluted with a mixture 1-butanol (5 parts), acetic acid (1 part) and water (1 part). The major peak was collected, evaporated to an oil, and lyophilized from dilute acetic acid to give 86 mg of the title compound as a white, fluffy powder. The product was homogeneous when examined by thin layer chromatography on silica gel in 4 different solvent systems when loads of 20–30 mcg were applied and spots visualized by Cl$_2$-starch reagent and Ehrlich reagent. The following Rf values were obtained: (A) 1-butanol:acetic acid:water (4:1:5, upper phase), 0.51; (B) ethyl acetate:-pyridine:acetic acid:water(20:5:13), 0.16; (C) 1-butanol:acetic acid:water:ethyl acetate (1:1:1:1), 0.66; (D) 1-butanol:pyridine:acetic acid:water (15:10:3:12), 0.65.

Amino acid analysis gave: Ser, 0.82; Pro, 1.09; Gly, 1.00; Leu, 1.01; Tyr, 1.05; Phe, 1.05; p-Cl-Phe, 0.97; Trp, 1.82; Arg, 1.08.

EXAMPLE 7

N-Acetyl-D-phenylalanyl-D-p-chlorophenylalanyl-D-tryptophyl-L-seryl-L-tyrosyl-D-tryptophyl-L-leucyl-L-arginyl-L-prolyl-glycinamide, [n-Ac-D-Phe$^1$, D-p-Cl-Phe$^2$, D-Trp$^{3,6}$]-LH-RH Removal of the protecting groups (with the exception of the N-acetyl variety) and the resin support (together with the anchoring radical) from the resin (0.73 g) described in Example 2 was accomplished under the conditions described in Example 6. The crude peptide was purified using the chromatography columns described in Example 6, except that 1-butanol:acetic acid:-water (6:1:1) was used for elution on silica gel. The lyophilized peptide, i.e. the title compound, was a white, fluffy powder (66 mg). The product was homogeneous when examined by thin layer chromatography on silica using the 4 solvent systems employed in Example 6 with the following Rf values: (A), 0.63; (B) 0.28; (C), 0.71; (D), 0.67.

Amino acid analysis gave: Ser, 0.85; Pro, 1.03; Gly, 0.99; Leu, 1.00; Tyr, 1.02; Phe, 1.01; p-Cl-Phe, 0.96; Trp, 1.83; Arg, 0.98.

EXAMPLE 8

D-Phenylalanyl-D-p-bromophenylalanyl-D-tryptophyl-L-seryl-L-tyrosyl-D-phenylalanyl-L-leucyl-L-arginyl-L-prolyl-gllycinamide, [D-Phe$^1$, D-p-Br-Phe$^2$, D-Trp$^3$, D-Phe$^6$]-LH-RH Removal of the protecting groups, and the resin support together with the anchoring radical, from the peptide resin (1.42 g) described in Example 3 was accomplished under the conditions described in Example 6. The crude peptide was purified using the chromatography columns described in Example 6 and the pure, lyophilized, fluffy white peptide weighed 203 mg. The product i.e. the title compound, was homogeneous when examined by thin layer chromatography on silica using the 4 solvent systems described in Example 6 with the following Rf values: (A), 0.48; (B), 0.54; (C), 0.79; (D), 0.59.

Amino acid analysis gave: Ser, 0.79; Pro, 0.94; Gly, 1.00; Leu, 1.02; Tyr, 0.94; Phe, 1.84; Trp, 0.93; Arg and p-Br-Phe, 1.84.

EXAMPLE 9

D-Phenylalanyl-D-p-chlorophenylalanyl-D-tryptophyl-L-tyrosyl-D-phenylalanyl-L-leucyl-L-arginyl-L-prolyl-glycinamide, [D-Phe$^1$, D-p-Cl-Phe$^2$, D-Trp$^3$, D-Phe$^6$]-LH-RH Removal of the protecting groups, and the resin support together with the anchoring radical, from the peptide-resin (0.76 g) described in Example 4 was accomplished under the conditions described in Example 6. The crude peptide was purified using the chromatography columns described in Example 6 except that 1-butanol:acetic acid:water (5:1:1) is used for elution on silica gel. The pure title compound was obtained as a fluffy, white powder (94 mg) after lyophilization. This product was homogeneous when examined by thin layer chromatography on silica plates using the solvent systems described in Example 6 with the following Rf values: (A), 0.42; (B), 0.46; (C), 0.72; (D), 0.60.

Amino acid analysis gave: Ser, 0.83; Pro, 0.94; Gly, 1.00; Leu, 1.01; Tyr, 0.93; Phe, 1.93; p-Cl-Phe, 0.95; Trp, 0.85; Arg, 0.98.

EXAMPLE 10

N-Succinyl-D-phenylalanyl-D-p-chlorophenylalanyl-D-tryptophyl-L-seryl-L-tyrosyl-D-phenylalanyl-L-leucyl-L-arginyl-L-prolyl-glycinamide, [N-Succ-D-Phe$^1$, D-p-Cl-Phe$^2$, D-Trp$^3$, D-Phe$^6$]-LH-RH Removal of the protecting groups (with exception of the N-succinyl group), and the resin support together with the anchoring radical, from the peptide-resin (0.75 g) described in Example 5 was accomplished under the conditions described in Example 6. The crude peptide was purified using the chromatography column and conditions described in Example 6. The pure title compound was obtained as a white, fluffy powder (78 mg) upon lyophilization. This material was homogeneous when examined by thin layer chromatography using the solvent systems described in Example 6. The following Rf values were obtained: (A), 0.52; (D), 0.71, 2-propanol: 1 molar acetic acid (2:1), 0.70; ethyl acetate:-pyridine:acetic acid:water (5:5:1:3), 0.94.

Amino acid analysis gave: Ser, 0.86; Pro, 0.98; Gly, 1.00; Leu, 1.09; Tyr, 1.06; Phe, 1.98; p-α-Phe, 0.97; Trp, 0.94; Arg, 1.01.

EXAMPLE 11

N-Acetyl-D-p-chlorophenylalanyl-D-p-chlorophenylalanyl-D-tryptophyl-L-seryl(O-benzyl)-L-tyrosyl-D-tryptophyl-L-leucyl-L-arginyl(N$^G$-tosyl)-L-prolylglycyl-benzhydrylamine resin The peptide resin was assembled on the same scale and under conditions described in Example 1, with the exception that t-Boc-D-p-chlorophenylalanine was incorporated into position one instead of t-Boc-D-phenylalanine and the decapeptide resin was acetylated under the conditions described in Example 2. The completed, acetylated, dry peptide resin (i.e. the title compound) weighed 1.58 g.

EXAMPLE 12

N-Acetyl-D-tryptophyl-D-p-chlorophenylalanyl-D-tryptophyl-L-seryl(O-benzyl)-L-tyrosyl-D-tryptophyl-L-leucyl-L-arginyl(N$^G$-tosyl)-L-prolyl-glycyl-benzhydrylamine resin The peptide resin was assembled on the same scale and under the same conditions described in Example 1, with the exception that t-Boc-D-tryptophan was incorporated into position 1 instead of t-Boc-D-phenylalanine. The completed, acetylated, dry peptide resin (i.e. the title compound) weighed 1.62 g.

EXAMPLE 13

N-Acetyl-D-phenylalanyl-D-p-chlorophenylalanyl-D-tryptophyl-L-seryl(O-benzyl)-L-tyrosyl-D-tryptophyl-L-leucyl-L-arginyl (N$^G$-tosyl)-L-prolyl-D-alanyl-benzhydrylamine resin The peptide resin was assembled on the same scale and under the same conditions described in Example 1, with the exception that t-Boc-D-alanine was incorporated instead of t-Boc-glycine and the decapeptide resin was acetylated under the conditions described in Example 2. The completed, acetylated, dry peptide resin (i.e. the title compound) weighed 1.61 g.

EXAMPLE 14

N-Acetyl-D-p-chlorophenylalanyl-D-p-chlorophenylalanyl-D-tryptophyl-L-seryl-L-tyrosyl-D-tryptophyl-L-leucyl-L-arginyl-L-prolyl-glycinamide, [N-Ac-D-p-Cl-Phe$^{1,2}$, D-Trp$^{3,6}$]LH-RH Removal of the protecting groups (with the exception of the N-acetyl variety), and the resin support with the anchoring radical, from the resin described in Example 11 was accomplished under the conditions described in Example 6, except that ethyl acetate:pyridine:acetic acid:water (17:5:1:3) is used for elution on silica gel. The lyophilized peptide, the title compound, is a white, fluffy powder (118 mg) which was homogeneous when examined by thin layer chromatography on silica in four solvent systems. The following Rf values were obtained: (A) 1-butanol:acetic acid:water (4:1:5, upper phase), 0.51; (B) 1-butanol:acetic acid:water:ethyl acetate (1:1:1:1), 0.83; (C) ethyl acetate:pyridine:acetic acid:water (5:5:1:3), 0.95; and isopropanol:2 M acetic acid (2:1), 0.72.

Amino acid analysis gave: Ser, 0.86; Pro, 1.00; Gly, 1.00; Leu, 1.02; Tyr, 0.93; p-Cl-Phe, 2.02; Trp, 1.40; Arg, 0.99.

EXAMPLE 15

N-Acetyl-D-tryptophyl-D-p-chlorophenylalanyl-D-tryptophyl-L-seryl-L-tryosyl-D-tryptophyl-L-leucyl-L-arginyl-L-prolyl-glycinamide, [N-Ac-D-Trp$^{1,3,6}$, D-p-Cl-Phe$^2$]-LH-RH Protecting groups and the resin support together with the anchoring radical, were removed from the resin described in Example 12. The free peptide purified under the conditions described in Example 14. The lyophilized peptide, the title compound, was a white, fluffy powder (88 mg) which was homogeneous on silica in four solvent systems. The following Rf values were obtained: (A) 1-butanol:acetic acid:water (4:1:5, upper phase), 0.52; (B) 1-butanol:acetic acid:water:ethyl acetate (1:1:1:1), 0.78; (C) ethyl acetate:acetic acid:water (20:5:1:3), 0.22; (D) isopropanol:2 M acetic acid (2:1), 0.70.

Amino acid analysis gave: Ser, 0.81; Pro, 0.97; Gly, 1.02; Leu, 1.03; Tyr, 1.03; p-Cl-Phe, 0.97; Trp, 3.06; Arg, 0.99.

EXAMPLE 16

N-Acetyl-D-phenylalanyl-D-p-chlorophenylalanyl-D-tryptophyl-L-seryl-L-tyrosyl-D-tryptophyl-L-leucyl-L-arginyl-L-prolyl-D-alaninamide, [N-Ac-D-Phe$^1$, D-p-Cl-Phe$^2$, D-Trp$^{3,6}$, D-Ala$^{10}$]-LH-RH Protecting groups and the resin support together with the anchoring radical, were removed from the resin described in Example 13. The free peptide purified under the conditions described in Example 14. The lyophilized peptide was a white, fluffy powder (159 mg) which was homogeneous in the four solvent systems described in Example 15: (A), 0.56; (B), 0.83; (C), 0.24; (D), 0.68.

Amino acid analysis gave: Ser, 0.88; Pro, 1.00; Ala, 1.06; Leu, 1.00; Tyr, 0.97; Phe, 0.95; p-Cl-Phe, 0.96; Trp, 2.08; Arg, 0.93.

EXAMPLE 17

D-Phenylalanyl-D-p-fluorophenylalanyl-D-tryptophyl-L-seryl (O-benzyl)-L-tyrosyl-D-phenylalanyl-L-leucyl-L-arginyl (N$^G$-tosyl)-L-prolyl-glycyl-benzhydrylamine resin The peptide resin was assembled on the same scale and under conditions described in Example 1, with the exception that t-Boc-D-fluorphenylalanine was incorporated in place of t-Boc-D-chlorophenylalanine and that t-Boc-phenylalanine was incorporated in place of t-Boc-D-tryptophan in position six of the chain. The completed, dry peptide resin of the title compound weighed 1.41 g.

EXAMPLE 18

D-Phenylalanyl-D-p-fluorphenylalanyl-D-tryptophyl-L-seryl-L-tyrosyl-D-phenylalanyl-L-leucyl-L-arginyl-L-prolyl-glycinamide, [D-Phe$^1$, D-p-F-Phe$^2$, D-Trp$^3$, D-Phe$^6$]-LH-RH Removal of the protecting groups and the resin support together with the anchoring radical, from the peptide resin (1.41 g) described in Example 17 was accomplished under the conditions described in Example 6. The crude peptide was purified using the chromatography columns described in Example 6 and the pure, lyophilized, fluffy white peptide weighed 153 mg. The product i.e. the title compound, was homogeneous when examined by thin layer chromatography on silica using the three solvent systems described in Example 15 with the following Rf values: (A) 0.48; (B) 0.81; (C) 0.53.

Amino acid analysis gave: Ser, 0.88; Pro, 1.03; Gly, 1.10; Leu, 1.00; Tyr, 0.98; Phe, 1.95; p-F-Phe, 0.98; Trp, 0.93; Arg, 1.02.

EXAMPLE 19

In the same manner as described in the previous examples the following peptides were prepared: N-Ac-D-p-Cl-Phe$^{1,2}$, D-Trp$^3$, D-Phe$^6$, D-Ala-$^{10}$-LH-RH; N-Ac-D-Trp$^1$, D-p-Cl-Phe$^2$, D-Trp$^3$, D-Phe$^6$, D-Ala$^{10}$-LH-RH; N-Ac-D-pF-Phe$^1$, D-p-Cl-Phe$^2$, D-Trp$^{3,6}$-D-Ala$^{10}$-LH-RH; N-Ac-Ala$^1$, D-p-Cl-Phe$^2$, D-Trp$^{3,6}$-D-Ala$^{10}$-LH-RH; N-Ac-D-Ala$^{1,10}$, D-p-Cl-Phe$^2$, D-Trp$^{3,6}$-LH-RH; N-Ac-Gly$^1$, D-p-Cl-Phe$^2$, D-Trp$^{3,6}$-D-Ala$^{10}$-LH-RH.

We claim:

1. A compound of formula I:

$$X-R^1-R^2-R^3-Ser-Tyr-R^4-Leu-Arg-Pro-R^5-NH_2 \qquad (I)$$

in which X is hydrogen, lower alkanoyl, HOOC-(CH$_2$)$_n$-CO wherein n is an integer from 2 to 6, benzoyl or the acyl portion of a D- or L-amino acid; R$^1$ is Gly,L-Ala,D-Ala, or D-Phe having a substituent in the para position of the phenyl group selected from the group consisting of nitro, amino, methyl, cyano, trifluoromethyl, hydroxy and methoxy; R$^2$ is D-Phe having a substituent in the para position of the phenyl group selected from the group consisting of halo, nitro, amino, methyl, cyano, trifluoromethyl, hydroxy and methoxy; R$^3$ is D-Trp,L-Trp or L-Phe; R$^4$ is D-Trp,D-Phe or D-Phe having a substituent in the para position of the phenyl group selected from the group consisting of halo, nitro, amino, methyl, cyano, trifluoromethyl, hydroxy and methoxy; and R$^5$ is Gly or D-Ala; or a therapeutically acceptable salt thereof.

2. The compound of claim 1, in which R$^5$ is D-Ala.

3. The compound of claim 1, in which X is hydrogen, lower alkanoyl, HOOC-(CH$_2$)$_n$-CO wherein n is an integer from 2 to 6, benzoyl or the acyl portion of an amino acid residue of alanine, arginine, asparagine, cysteine, glutamine, glycine, histidine, isoleucine, leucine, lysine, methionine, ornithine, phenylalanine, proline, serine, threonine, tryptophan, tyrosine or valine; $R^1$ is D-p-Y-Phe wherein Y is selected from the group consisting of nitro, amino, methyl, cyano, trifluoromethyl, hydroxy and methoxy; $R^2$ is D-p-Y-Phe in which Y is as defined herein; $R^3$ is D-Trp; $R^4$ is D-Trp, D-Phe or D-p-Y-Phe in which Y is as defined herein; and $R^5$ is D-Ala; or a therapeutically acceptable salt thereof.

4. The compound of claim 1, in which X is hydrogen, lower alkanoyl or $HOOC\text{-}(CH_2)_n\text{-}CO$ wherein n is an integer from 2 to 6; $R^2$ is D-p-halo-Phe; $R^3$ is D-Trp; $R^4$ is D-Trp or D-Phe; and $R^5$ is D-Ala; or a therapeutically acceptable salt thereof.

5. The compound of claim 1, in which X is acetyl or $HOOCCH_2\text{-}CH_2CO$, $R^2$ is D-p-Cl-Phe; D-p-Br-Phe or D-p-F-Phe; $R^3$ is D-Trp; $R^4$ is D-Trp or D-Phe; and $R^5$ is D-Ala; or a therapeutically acceptable salt thereof.

6. A gonadotropin antagonizing pharmaceutical composition comprising a gonadotropin antagonizing amount of the compound of claim 1 or a therapeutically acceptable salt thereof, and a pharmaceutically acceptable carrier.

7. The compound of claim 1 which is N-Ac-Ala$^1$, D-p-Cl-Phe$^2$, D-Trp$^{3,6}$-D-Ala$^{10}$-LH-RH.

8. The compound of claim 1 which is N-Ac-D-Ala$^{1,10}$,-D-p-Cl-Phe$^2$,D-Trp$^{3,6}$-LH-RH.

9. The compound of claim 1 which is N-Ac-Gly$^1$,-D-p-Cl-Phe$^2$,D-Trp$^{3,6}$-D-Ala$^{10}$-LH-RH.

* * * * *